US009647266B2

(12) United States Patent
Vaughey et al.

(10) Patent No.: US 9,647,266 B2
(45) Date of Patent: May 9, 2017

(54) AMORPHOUS TITANIA/CARBON COMPOSITE ELECTRODE MATERIALS

(71) Applicant: UCHICAGO ARGONNE, LLC, Chicago, IL (US)

(72) Inventors: John T. Vaughey, Elmhurst, IL (US); Andrew Jansen, Bolingbrook, IL (US); Christopher D. Joyce, Columbus, OH (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 0 days.

(21) Appl. No.: 14/523,431

(22) Filed: Oct. 24, 2014

(65) Prior Publication Data

US 2015/0044542 A1 Feb. 12, 2015

Related U.S. Application Data

(62) Division of application No. 12/914,197, filed on Oct. 28, 2010, now Pat. No. 8,871,374.

(51) Int. Cl.
*H01M 4/36* (2006.01)
*C01G 23/047* (2006.01)
(Continued)

(52) U.S. Cl.
CPC .......... *H01M 4/366* (2013.01); *C01G 23/047* (2013.01); *C07F 7/006* (2013.01); *H01M 4/131* (2013.01);
(Continued)

(58) Field of Classification Search
CPC ...... H01M 4/625; H01M 4/485; H01M 4/587; H01M 10/0525; H01M 4/131;
(Continued)

(56) References Cited

U.S. PATENT DOCUMENTS 6,221,531 B1  4/2001  Vaughey et al.
6,770,257 B1  8/2004  Imura et al.
(Continued)

OTHER PUBLICATIONS

M. Anji Reddyet al., Crystallite Size Constraints on Lithium Insertion into Brookite TiO2, Electrochemical and Solid State Letters, 11 (8) A132-A134 (2008).
(Continued)

*Primary Examiner* — Mark F Huff
*Assistant Examiner* — Monique Wills
(74) *Attorney, Agent, or Firm* — Olson & Cepuritis, Ltd (57) ABSTRACT

An isolated salt comprising a compound of formula $(H_2X)(TiO(Y)_2)$ or a hydrate thereof, wherein X is 1,4-diazabicyclo[2.2.2]octane (DABCO), and Y is oxalate anion ($C_2O_4^{-2}$), when heated in an oxygen-containing atmosphere at a temperature in the range of at least about 275° C. to less than about 400° C., decomposes to form an amorphous titania/carbon composite material comprising about 40 to about 50 percent by weight titania and about 50 to about 60 percent by weight of a carbonaceous material coating the titania. Heating the composite material at a temperature of about 400 to 500° C. crystallizes the titania component to anatase. The titania materials of the invention are useful as components of the cathode or anode of a lithium or lithium ion electrochemical cell.

5 Claims, 6 Drawing Sheets

(51) Int. Cl.
- C07F 7/00 (2006.01)
- H01M 4/485 (2010.01)
- H01M 4/587 (2010.01)
- H01M 10/0525 (2010.01)
- H01M 4/131 (2010.01)
- H01M 4/133 (2010.01)
- H01M 4/48 (2010.01)
- H01M 4/62 (2006.01)

(52) U.S. Cl.
CPC ........... H01M 4/133 (2013.01); H01M 4/364 (2013.01); H01M 4/483 (2013.01); H01M 4/485 (2013.01); H01M 4/587 (2013.01); H01M 4/625 (2013.01); H01M 10/0525 (2013.01); C01P 2002/72 (2013.01); C01P 2002/88 (2013.01); C01P 2004/03 (2013.01); C01P 2006/40 (2013.01); Y02E 60/122 (2013.01)

(58) Field of Classification Search
CPC ............. C01P 2002/88; C01P 2006/40; C01G 23/047; Y02E 60/122
USPC ............................ 429/218.1, 231.8, 231.95
See application file for complete search history.

(56) References Cited

U.S. PATENT DOCUMENTS

| | | | |
|---|---|---|---|
| 7,175,825 B2 | 2/2007 | Nakano et al. | |
| 7,255,847 B2 | 8/2007 | Daoud et al. | |
| 7,465,520 B2 | 12/2008 | Belharouak et al. | |
| 2012/0231352 A1* | 9/2012 | Pol | B82Y 30/00 429/341 |

OTHER PUBLICATIONS

Erin M. Sorensen et al., Three-Dimensionally Ordered Macroporous Li4Ti5O12: Effect of Wall Structure on Electrochemical Properties, Chem. Mater. (18) 482-489 (2006).
C.H. Chen et al., Studies of Mg-Substituted Li4-xMgxTi5O12 Spinel Electrodes . . . Journal of the Electrochemical Society, 148 (1), A102-A104 (2001).
Antonino S. Arico et al., Nanostructured Materials for Advanced Energy Conversion and Storage Devices, Nature Materials, (4) 366-377(2005).
A.K. Padhi et al., Phospho-olivines as Positive-Electrode Materials for Rechargeable Lithium Batteries, J. Electrochem. Soc. (144) No. 4, 1188-1194 (1997).
Yong-Sheng Hu et al., High Lithium Electroactivity of Nanometer-Sized Rutile TiO2, Adv. Mater., (18) 1421-1426 (2006).
A. Robert Armstrong et al., Adv. Mater., (17) No. 7, 862-865 (2005).
Guillaume Sudant et al., Electrochemical Lithium Reactivity with Nanotextured Anatase-type TiO2, J. Mater. Chem. (15) 1263-1269 (2005).
M. M. Doeff et al., Effect of Surface Carbon Structure on the Electrochemical Performance of LiFePO4, Electrochemical and Solid State Letters, 6 (10) A207-A209 (2003).
Crystal D. May et al., New Cathode Materials for Silver-Based Primary Batteries: AgCuO2 and Ag2Cu2O3, Electrochemistry Communications 6, 1075-1079 (2004).
Peter G. Bruce et al., Nanomaterials for Rechargeable Lithium Batteries, Angew. Chem. Int. Ed. (47), 2930-2946 (2008).
Sara Nordlinder et al., Lithium Insertion into Vanadium Oxide Nanotubes: Electrochemical and Structural Aspects, Chem. Mater. 18, 495-503 (2006).
Marcos Fernandez-Garcia et al., Anatase-TiO2 Nanomaterials: Analysis of Key Parameters Controlling Crystallization, J. Am. Chem. Soc. 129, 13604-13612 (2007).
Xiaoxu Li et al., Large-Scale Fabrication of TiO2 Hierarchical Hollow Spheres, Inorganic Chemistry, (45) No. 9, 3493-3495 (2006).
John Wang et al., Pseudocapacitive Contributions to Electrochemical Energy Storage in TiO2 (Anatase) Nanoparticles, J. Phys. Chem. C, 111, 14925-14931 (2007).
Hiroyasu Furukawa et al., Electrochemical Properties of Nanostructured Amorphous, Sol-gel Synthesized . . . , Journal of the Electrochemical Society, 151 (4) A527-A531 (2004).
Cristiana Di Valentin et al., Characterization of Paramagnetic Species in N-Doped TiO2 Powders by EPR . . . J. Phys. Chem. B, (109) No. 23, 11414-11419 (2005).
Chunhai Jiang et al., Particle Size Dependence of the Lithium Storage Capability and High Rate Performance of Nanocrystalline . . . , Journal of Power Sources 166, 239-243 (2007).
Liam D. Noailles et al., Lithium Insertion Into Hollandite-type TiO2, Journal of Power Sources, 81-82, 259-263 (1999).
M. Anji Reddy, Lithium Intercalation Into Nanocrystalline Brookite TiO2, Electrochemical and Solid State Letters, 10 (2) A29-A31 (2007).
M. Anji Reddy, Room Temperature Synthesis and Li Insertion into Nanocrystalline Rutile TiO2, Electrochemistry Communications (8) 1299-1303 (2006).
K.S. Rane, Visible Light-Sensitive Yellow TiO2-xNx and Fe—N Co-Doped Ti1-yFeyO2-xNx Anatase Photocatalysts, Journal of Solid State Chemistry (179), 3033-3044 (2006).
A. Fester et al., Crystal Structure of Cesium-bis (Oxalato) Oxo-Titanate (IV) Hydrate, Inorganica Chimica Acta, (193) 99-103 (1992).
Y. V. Kolen'ko et al., Phase Composition of Nanocrystalline Titania Synthesized under Hydrothermal Conditions from Different . . . , Inorganic Materials (40) 8, 822-828 (2004).
A Fester et al., Dipotassium Bis(oxalato)oxotitanate(IV) Dihydrate, Acta Cryst. C50, 850-852 (1994).
X.L. Yao et al., Comparisons of Graphite and Spinel Li1.33Ti1.67O4 as Anode Materials for Rechargeable Lithium-Ion Batteries, Electrochimica Acta 50 4076-4081 (2005).
M. C.Tsai et al., Lithium Ion Intercalation Performance of Porous Laminal Titanium Dioxides Synthesized by Sol-Gel Process, Chem. Mater. 21, 499-505 (2009).
Charles R. Sides et al., A High-Rate, Nanocomposite LiFePO4/Carbon Cathode, Electrochemical and Solid State Letters, 8(9) A484-A487 (2005).
M. Latroche et al., New Hollandite Oxides: TiO2(H) and K0.06TiO2, Journal of Solid State Chemistry 81, 78-82 (1989).
Christopher D. Joyce et al., Synthesis and Electrochemical Evaluation of an Amorphous Titanium Dioxide . . . Journal of Power Sources 195, 2064-2068 (2010).

* cited by examiner

AMORPHOUS TITANIA/CARBON COMPOSITE ELECTRODE MATERIALS

CROSS-REFERENCE TO RELATED APPLICATIONS

This application is a division of U.S. application Ser. No. 12/914,197, filed on Oct. 28, 2010, which is incorporated herein by reference in its entirety.

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to titanium oxides and methods of preparing the same. More particularly, this invention relates to amorphous titania (titanium dioxide) and composites thereof with carbon, precursors of the titania materials, electrode materials comprising the titania/carbon composites, as well as methods of preparing amorphous titania/carbon composites and other isoforms of titania from the precursor materials.

BACKGROUND

Titanium dioxide is an important material used in many industrial and scientific applications. For example, titanium oxides are an important class of lithium-ion battery electrodes owing to their good capacity and stability within the cell environment. In addition to several naturally occurring polytypes (e.g., brookite, anatase, and rutile), several manmade polymorphs reportedly have been synthesized via ion-exchange, notably $TiO_2(B)$ from $K_2Ti_4O_9$ and $TiO_2(H)$ from $K_2Ti_8O_{16}$ [1-13]. The particular polytype isolated from a given synthetic process is dependant on variables that include, e.g., the precursor material or materials used to prepare the titanium oxide, the temperature at which the titanium oxide material is produced, and the atmosphere utilized during the production process. Low temperature preparations (e.g., <100° C.) typically yield brookite. Titanium oxide materials prepared above 700° C. generally yield rutile. Anatase generally is isolated from processes run at temperatures between 100 and 700° C. For titanium dioxide materials prepared or annealed under an ammonia atmosphere, nitrogen-doped yellow anatase or rutile has been isolated and characterized [14, 15]. As bulk materials, rutile is electrochemically inactive, brookite inserts about 0.16 Li per formula unit, while anatase, $TiO_2(H)$ and $TiO_2(B)$ insert about 0.5 Li per formula unit [1,2,7,10]. These differences reflect the different arrangements of the titanium centered octahedral within the crystal structures of the materials and the resultant internal void spaces that are present in the crystal structure. Significant differences and levels of activity have been reported when nanoscale versions of the titanium dioxide materials are evaluated, reflecting the smaller diffusion distances and increasing important role of surfaces [16, 17, 18].

Although most Ti(IV) oxides are poor electronic conductors, new methods developed to synthesize small particle size (e.g., nanometer scale) primary particles have achieved the higher rate capability needed for modern commercial applications. Consequently, there is an ongoing need to develop new methods for synthesizing the various forms of titanium oxides. This need is addressed by the present invention.

SUMMARY OF THE INVENTION

The present invention relates, in part, to an isolated salt comprising a compound of formula $(H_2X)(TiO(Y)_2)$ or a hydrate thereof, wherein X is 1,4-diazabicyclo[2.2.2]octane (DABCO), and Y is oxalate anion $(C_2O_4^{-2})$. When the salt is heated in an oxygen-containing atmosphere (e.g., air) at a temperature of at least about 275° C. and less than about 400° C., the salt decomposes to form an amorphous titania/carbon composite material comprising about 40 to about 50 percent by weight titania and about 50 to about 60 percent by weight of a carbonaceous material coating the titania.

In one preferred embodiment the salt has the formula: $(H_2DABCO)TiO(C_2O_4)_2 \cdot 2H_2O$. Heating this salt in an oxygen-containing atmosphere (e.g., air) at a temperature of less than 400° C., but at least about 275° C., for a period of time sufficient to result in a mass loss of at least about 45 percent by weight, produces a particulate amorphous titanium dioxide (titania) material as a composite with carbon. The composite comprises amorphous titania particles coated with a carbonaceous material (e.g., predominately carbon). The particles of the composite material typically have an average particle size in the range of about 25 to about 35 micrometers (e.g., about 30 micrometers). Heating the amorphous titania/carbon composite at a temperature in the range of about 400° C. to about 500° C. causes the titania in the composite sufficient to crystallize to anatase. The resulting anatase material has a surprisingly higher electrochemical capacity when used as the anode in a lithium or lithium ion cell, compared to commercial anatase.

The titania/carbon composite material and anatase materials of the present invention are useful as components of the anode of a lithium or lithium ion electrochemical cell, either alone, or in combination with a lithiated metal oxide material, such as $Li_4Ti_5O_{12}$, and the like. In addition, the amorphous and anatase titania/carbon composite materials of the present invention can be utilized in other applications, e.g., photoelectric cells, solar cells, and catalysis.

BRIEF DESCRIPTION OF THE DRAWINGS

The invention consists of certain novel features and a combination of parts hereinafter fully described, illustrated in the accompanying drawings, it being understood that various changes in the details may be made without departing from the spirit, or sacrificing any of the advantages of the present invention.

DETAILED DESCRIPTION OF THE PREFERRED EMBODIMENTS

In one aspect, the present invention provides an isolated salt comprising a compound of formula $(H_2X)(TiO(Y)_2)$ or a hydrate thereof, wherein X is 1,4-diazabicyclo[2.2.2]octane (DABCO), and Y is oxalate anion $(C_2O_4^{-2})$. Preferably, the salt has the formula $(H_2DABCO)(TiO(C_2O_4)_2) \cdot 2H_2O$.

In another aspect, the present invention provides a method of preparing an amorphous titania/carbon composite material. The method comprises heating the isolated salt of formula $(H_2X)(TiO(Y)_2)$ or a hydrate thereof in an oxygen-containing atmosphere at a temperature in the range of at least about 275 to less than 400° C. (e.g., about 350° C.) for a period of time (e.g., about 8 to 12 hours) sufficient to achieve a mass loss of at least about 45 percent by weight (e.g., about 10 to 12 hours). The resulting product comprises a particulate amorphous titania/carbon composite material comprising about 40 to about 50 percent by weight of amorphous titania and about 50 to about 60 percent by weight of a carbonaceous material (e.g., predominately carbon) coating the titania. Preferably, the amorphous titania is free from detectable crystalline forms of titania as determined by powder X-ray diffraction techniques. The titania/carbon composite material typically has an average particle size in the range of about 25 to about 35 micrometers.

In another aspect, the present invention provides a method of preparing an anatase material comprising heating the amorphous titania/carbon composite described above at a temperature in the range of about 400° C. to about 500° C. for a period of time sufficient to crystallize the majority of the titania in the composite to anatase. A preferred method of preparing anatase comprises heating the isolated $(H_2DABCO)(TiO(C_2O_4)_2)$ salt or hydrate thereof in an oxygen-containing atmosphere at a temperature in the range of about 400 to about 500° C. for a period of time sufficient to achieve a mass loss of at least about 45 percent by weight forming a titania material, and to crystallize the majority of the titania to anatase. The anatase material formed by these processes has surprising and unique electrochemical properties (e.g., higher capacity) when used as a anode component in a lithium or lithium ion cell, compared to commercial anatase.

In another aspect, the present invention provides a anode for a lithium or lithium ion electrochemical cell. The anode comprises a particulate amorphous titania/carbon composite material or anatase material as described above, either alone, or in combination with a lithium-containing metal oxide material, such as $Li_4Ti_5O_{12}$. The anode can be included in an electrochemical cell along with a cathode (e.g., a lithium metal-containing material), and a lithium ion-containing electrolyte (e.g., a lithium salt in a non-aqueous liquid medium). The cathode and electrolyte materials for lithium and lithium ion electrochemical cells are well known in the art. A battery can be constructed from a plurality of such electrochemical cells arranges in series, in parallel, or both. Anodes, electrochemical cells, and batteries can also be formed from the anatase materials of the present invention. In the case where lithium metal is used as an anode, the titanium dioxide materials of the present invention can be used as a cathode material, if desired.

The following non-limiting examples are provided to further illustrate various aspects and features of the materials and methods of the present invention.

EXAMPLE 1

Preparation of $(H_2DABCO)(TiO(C_2O_4)_2) \cdot 2H_2O$

The synthesis of titanyl-oxalato anion, $[TiO(C_2O_4)_2 \cdot xH_2O]^{2-}$, has been reported in the literature starting from the slow hydrolysis of $TiCl_4$ [19]. Due to the problems associated with working with titanium tetrachloride, the synthesis was modified to use titanium isopropoxide, $Ti(OC_3H_7)_4$ (Aldrich, 97%). In a typical synthesis, about 50 ml of $NH_4OH$ (Aldrich, 29.2% solution) was added to about 25 ml of $Ti(OC_3H_7)_4$, producing a white gelatinous precipitate. The precipitate was washed three times to remove excess base and placed in about 100 ml of de-ionized water. About 200 ml of a 0.23M solution of oxalic acid (Aldrich, 99.9%) was added producing a clear solution of $H_2[TiO(C_2O_4)_2]$. An approximately stoichiometric amount of an aqueous solution of DABCO (1,4-diazabicyclo[2.2.2]octane) (Aldrich, 98%) was added to the clear solution, thereby precipitating $(H_2DABCO)(TiO(C_2O_4)_2) \cdot 2H_2O$ as a white crystalline solid.

Thermogravimetric analysis (TGA) of the isolated crystalline solid salt, $(H_2DABCO)(TiO(C_2O_4)_2) \cdot 2H_2O$, was performed using a Seiko X-star 6300 TGA/DTA. Data were collected under flowing dry air atmosphere to determine water content and the temperature of decomposition for the material. The structures of the compounds produced during the TGA procedure were determined by powder X-ray diffraction of the products produced by annealing the precursor at a variety of temperatures under air. Data collected on a Siemens D5000 Powder X-ray Diffractometer was used to determine the type and purity of the titanium dioxide produced.

Scanning Electron Microscopy (SEM) images of the titanium dioxide materials were acquired utilizing an FEI Quanta 400 FEG Scanning Electron Microscope operating at 12.5 KV, under high vacuum mode. The SEM images were recorded with the Quanta xT microscope control software, version 2.4. Prior to image acquisition, the samples were sputter-coated using a Bal-Tec MED020 sputter coater with 10 nm of Au/Pd to prevent charging.

EXAMPLE 2

Electrochemical Evaluations

Electrodes were prepared comprising about 80% (active) of the titanium dioxide materials laminated on aluminum foil together with about 10% poly(vinylidene difluoride) binder (PvDF) and about 10% acetylene black as a conductive additive. Electrochemical cells (2032-type cells) were constructed using the titanium dioxide electrodes as the cathode, a lithium metal anode, and an electrolyte comprising 1.2M $LiPF_6$ in 3:7 EC:EMC [20]. The cells were cycled in the range of about 0.7-4.2 V using a constant current (about 0.08 mA or 0.05 mA/cm$^2$) on a MACCOR cycler. In addition, a mixture of the amorphous titanium dioxide/carbon composite (350° C.) was blended (1:2) with a sample of $Li_4Ti_5O_{12}$ and evaluated in the voltage window of about 1.0-2.0 V (at about 0.05 mA/cm$^2$).

RESULTS AND DISCUSSION

Building on previous work in developing low temperature preparations for electrochemically active titanium oxides, the present inventors sought to develop an air stable microcrystalline single source precursor to nanoscale titanium dioxide [19]. In addition to electrochemical interest, such a precursor would be useful as a source of active titanium dioxide for the synthesis of various titanium-based materials where the particle morphology needs to be maintained. For electrode materials based on titanium (IV) oxides, numerous studies have shown that doping or reducing the particle size of the titanium dioxide, significantly increases the rate capability [1,15,21]. Synthetic procedures starting from the simple dioxide usually require a high temperature heating step (with resulting loss of surface area) that may lead to an undesirable side reaction with the reaction vessel, or for battery materials evaporation of lithia.

Figure 1:
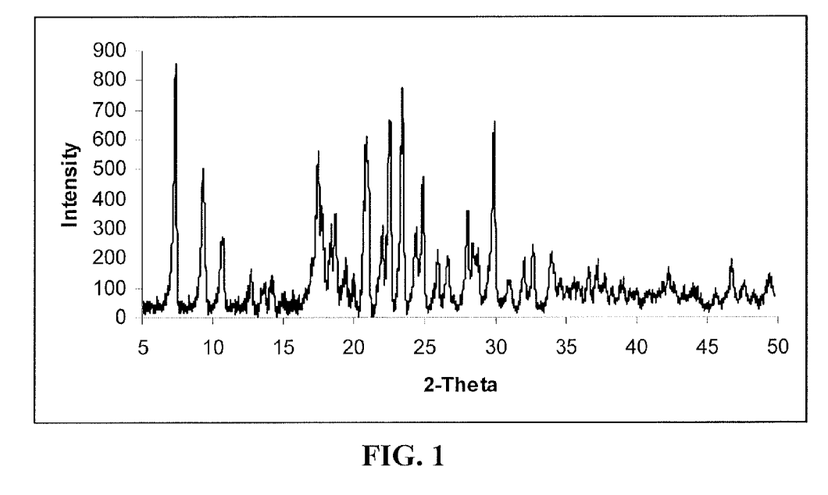
FIG. 1 depicts the powder X-ray diffraction pattern for $(H_2DABCO)TiO(C_2O_4)_2 \cdot 2H_2O$.
Figure 2:
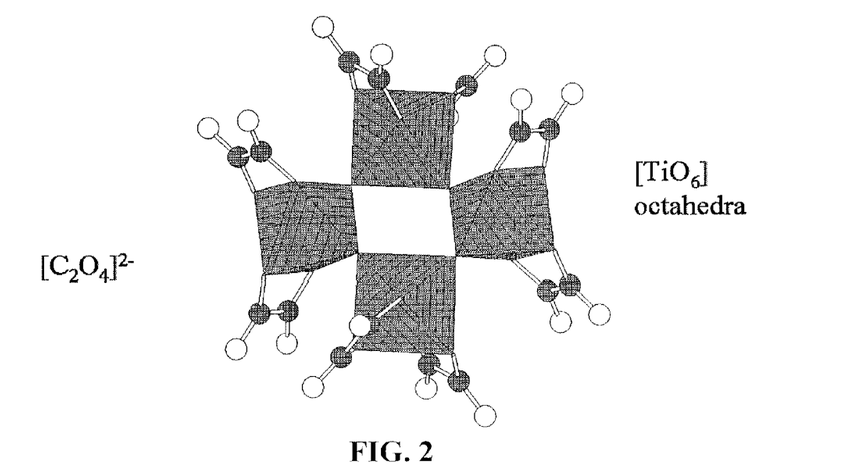
FIG. 2 depicts the tetramer of the $[TiO(C_2O_4)_2]^{-2}$ anion from $K_2[TiO(C_2O_4)_2]$; the small gray spheres are carbon, the open spheres are oxygen, and the hatched polyhedra are $[TiO_6]$.

According to the present invention, a solution of the titanyl-oxalato anion was prepared starting from titanium isopropoxide. The large organic base DABCO (1,4-diazabicyclo[2.2.2]octane) was added to an acidified solution of the anion, which resulted in precipitation of a titanyl-oxalato-DABCO salt: $(H_2DABCO)(TiO(C_2O_4)_2).x\ H_2O$. The X-ray powder diffraction pattern of the salt is shown in FIG. 1. Earlier crystallographic studies on the potassium salt by Fetser et al. showed that the titanyl-oxalato anion existed as a tetramer in the solid state, shown in FIG. 2 [22, 23]. Addition of other divalent counter-cations, such as Mn(II) or Ni(II), resulted in decomposition and precipitation of the simple oxalate salt, $M(C_2O_4).H_2O$, while alkali metal salts were too soluble and were isolated by solvent evaporation [19, 22]. Consequently, the suitability of DABCO ion as the counter-ion for the titanyl-oxalato salt was not evident from the prior art. Fortunately, the DABCO salt turned out to be surprisingly stable.

Figure 3:
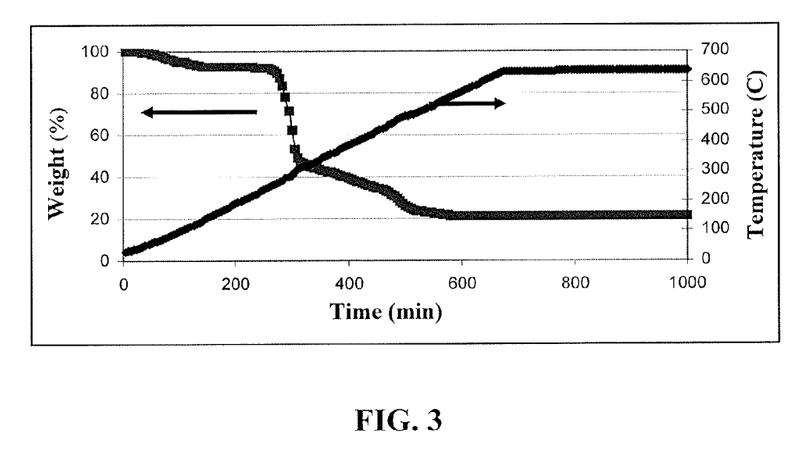
FIG. 3 depicts the thermogravimetric analysis (TGA) pattern for $(H_2DABCO)TiO(C_2O_4)_2 \cdot 2H_2O$.

The decomposition of the $(H_2DABCO)(TiO(C_2O_4)_2).x\ H_2O$ salt was studied by thermogravimetric analysis (TGA) under an air atmosphere. The data, shown in FIG. 3, indicated a weight loss of about 10% at a temperature of about 100° C., a large weight loss (about 45%) at about 275° C., and a gradual weight loss, completed by about 500° C., that corresponded to a loss of about 25% of the overall total weight loss. The weight loss at 100° C. corresponds to the loss of about 2.0 waters of hydration, indicating that the isolated salt is the dihydrate. The sharp drop at about 275° C. is mainly from decomposition of the oxalate fragments, and the final weight loss is close to that expected from loss of the DABCO cation.

Figure 4:
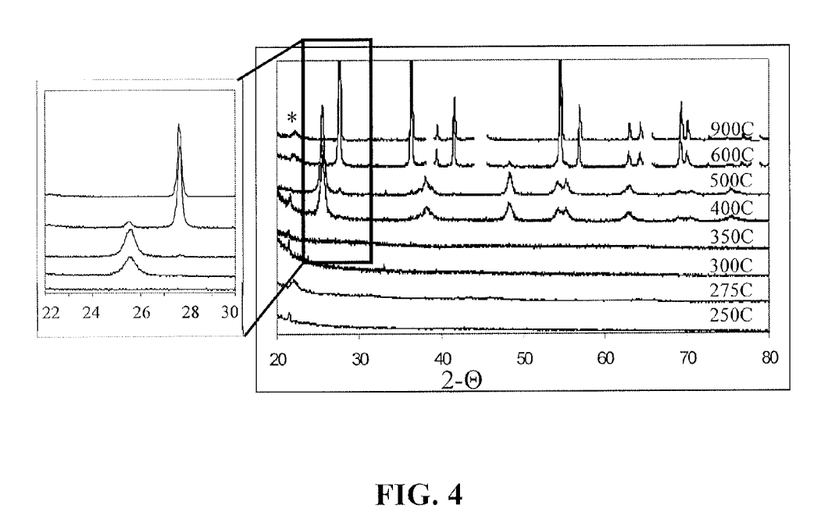
FIG. 4 depicts XRD patterns of the $TiO_2$ produced by the decomposition of $(H_2DABCO)TiO(C_2O_4)_2 \cdot 2H_2O$ at different temperatures; sample holder peaks were removed for clarification (* carbon); inset shows the shift from anatase to rutile as temperature increases.

The structures of the crystalline products of the decomposition were determined by heating of the salt at eight different temperatures between 300 and 900° C. in air for about 12 hours. Samples heated below 400° C. were found to be amorphous by X-ray diffraction methods. The materials isolated were black in color owing to the carbon produced from the incomplete decomposition of the DABCO cation. The 400° C. and 500° C. samples were found to be essentially single phase anatase. Scherrer equation calculations indicated a primary particle size of approximately 500 nm for both materials. The 400° C. sample was black and the 500° C. sample was yellow. The samples heated above 600° C. were white. The 600° C. sample contained mainly rutile with a few percent anatase, while the 900° C. product had rutile as the only detectable product. The XRD patterns are shown in FIG. 4.

Figure 5:
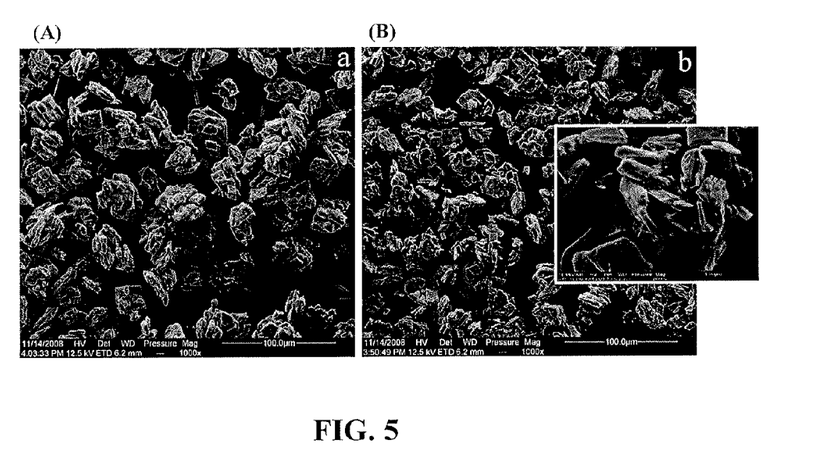
FIG. 5 depicts SEM images of (A) amorphous $TiO_2$ (350° C.) and (B) N-doped $TiO_2$ (500° C.).

FIG. 5 shows SEM images of a typical 350° C. sample (Panel (A), left), and a typical 500° C. sample (Panel (B), right). Both samples show similar morphology, i.e. roughly rectangular and flat particles fused together to form larger particles of irregular shape. The average particle size of the secondary particles for the 350° C. sample was approximately 50% larger (about 30 μm), than the 500° C. sample (about 20 μm). The inset in FIG. 5 shows an enlargement of the 500° C. particles highlighting the overall plate-like morphology. The reduced particle size for the sample heated to higher temperature likely reflects a particle breakdown that occurred upon completion of the decomposition of the DABCO cation (as seen in the TGA data) and the loss of remaining organic compounds.

Figure 6:
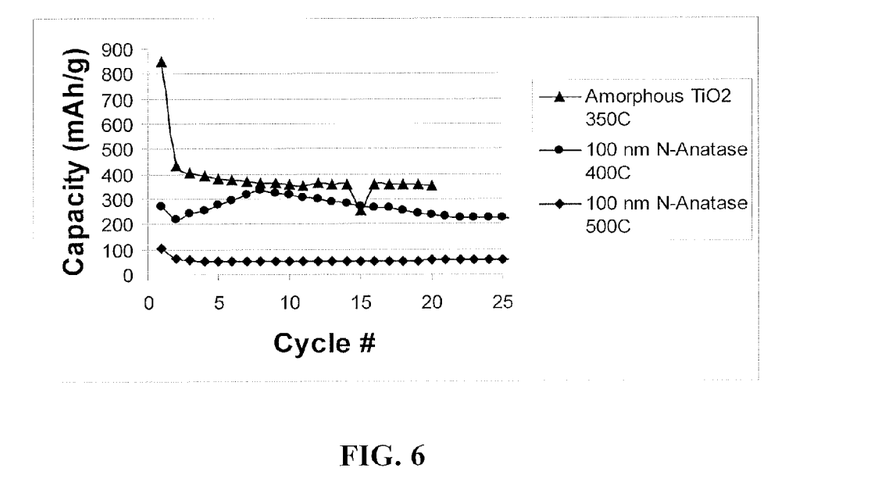
FIG. 6 depicts cycling performance of the various nanoscale $TiO_2$ samples.
Figure 7:
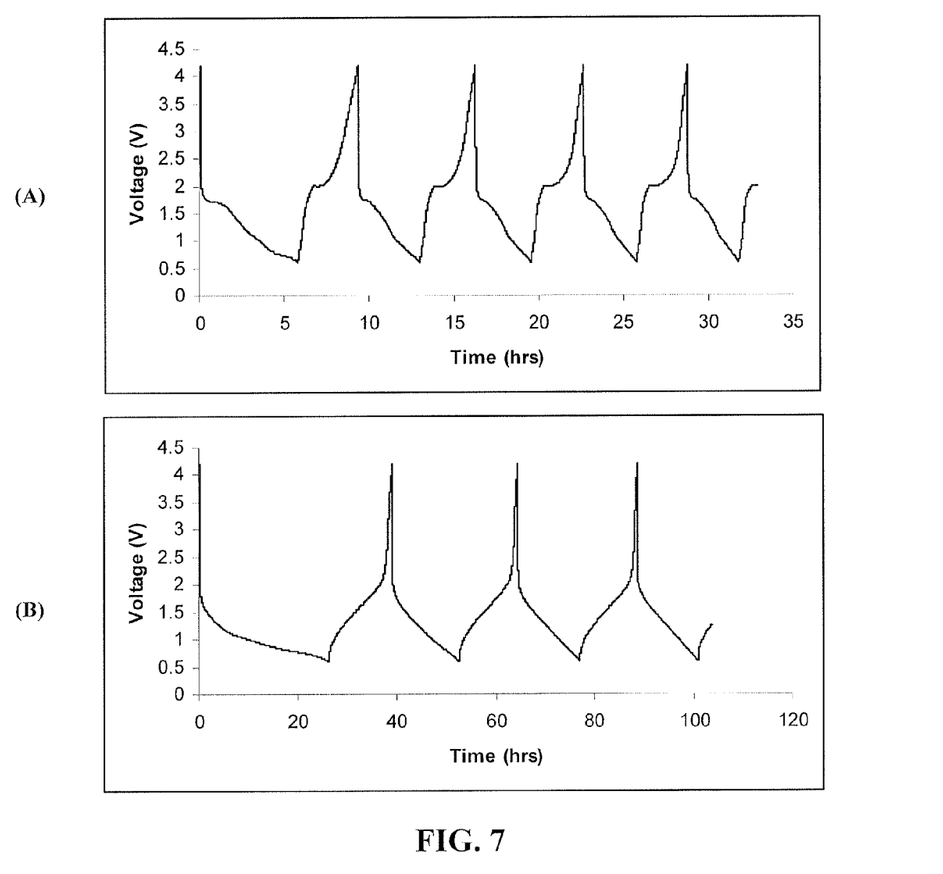
FIG. 7 depicts cycling profiles of (A) anatase produced at 500° C.; and (B) the amorphous $TiO_2$ sample produced at 350° C.
Figure 8:
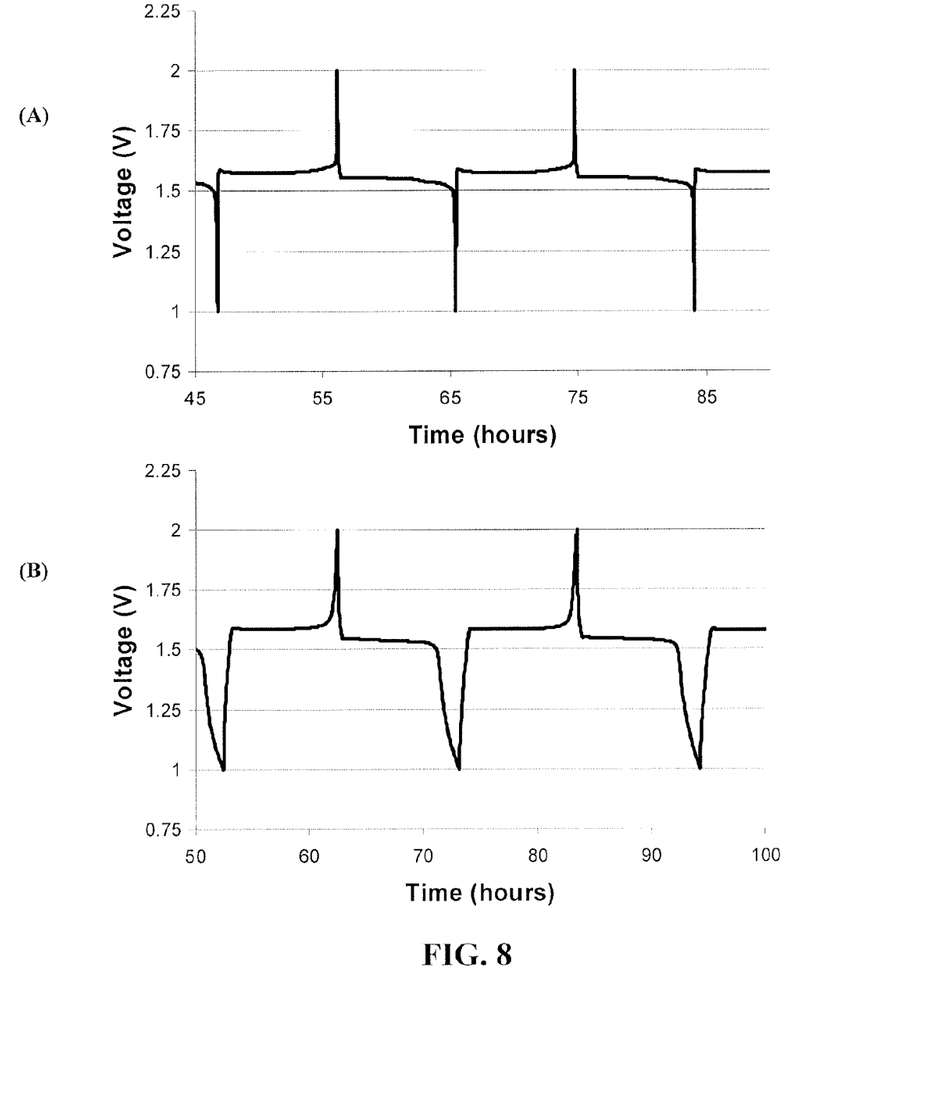
FIG. 8 depicts two cycles of (A) a 1:2 blend of the amorphous $TiO_2$ and $Li_4Ti_5O_{12}$ and (B) $Li_4Ti_5O_{12}$ alone.

Numerous titanium oxides and lithium titanium oxides are currently under study as next generation anodes for lithium ion batteries [3, 7]. Studies have shown that for titanium oxides, reducing the particle size increases rate capability, and in some instances, the capacity [1, 6, 13, 14, 24, 25]. The amorphous sample (350° C.) and the anatase samples (400° C., 500° C.) were evaluated electrochemically, and the data are shown in FIG. 6. Of the samples evaluated, the 350° C. amorphous sample showed the highest stable cycling capacity, surprisingly about 350 mAh/g, which is equal to about 1.0 $Li/TiO_2$, taking into account the carbon residue from the incomplete decomposition of the precursor salt. As isolated, the material is a mixture of about 55 wt % carbon and about 45 wt % $TiO_2$, the capacity of which is approximately 160 mAh/g. The cycling capacity of the anatase (400° C.) sample stabilized at about 210 mAh/g, while the 500° C. sample yielded about 50 mAh/g. A comparison of the cycling profiles for the anatase (A, 500° C.) and amorphous (B) titanium dioxide is shown in FIG. 7. The 500° C. sample exhibited approximately 2.0 V insertion plateaus characteristic of anatase, while the amorphous sample lacked these features. The lack of plateaus (even on cycling) and powder XRD data are consistent with the lack of a crystalline anatase component to the amorphous material. The observed capacity of the amorphous $TiO_2$/carbon mixture, mainly between about 1 to 2 V vs. lithium, is comparable to $Li_4Ti_5O_{12}$, and if used as a mixture, could act as a state of charge indicator for the electrode by adding a slight slope to the discharge curve [20, 21]. This effect is demonstrated in FIG. 8, where top Panel (A) shows the cycling profile of the blend, and bottom Panel (B) shows the profile for $Li_4Ti_5O_{12}$ alone.

It can be readily seen that on heating to 400° C., the amorphous $TiO_2$ component of the amorphous phase crystallizes to anatase resulting in a drop in cycling capacity. This capacity difference, taken as the $TiO_2$ component alone, is consistent with the reported capacity of anatase. Based on the TGA data, the 350° C. sample comprises about 55% carbon, while the 400° C. sample comprises 40% carbon. The 500° C. sample appears to lack any carbon. The high irreversible capacity of the amorphous sample (about 50%) probably arises from lithium reduction of the partially reduced organic components.

The drop in capacity between the carbon-coated anatase (400° C.) and the N-doped anatase (500° C.) is large—nearly 75%. Although the sample appears to have the typical cycling profile of anatase, it is not being completely utilized after burn-off of the carbon coating from the DABCO cation. It is possible that this 500° C. $TiO_2$ sample has poor ionic conductivity owing to the presence of nitrogen anions in the lattice and charge compensating protons in the central channel [26]. In a situation similar to the olivine cathode material $LiFePO_4$, poor lithium conductivity in the stoichiometric uncoated material results in a low cycling capacity [27]. Numerous studies on carbon coating titanium oxide materials, ex situ or in situ, show that as little as a few percent carbon, when properly applied, can result in realization of full theoretical capacity of the titanium oxide [28, 29].

A new air and water stable titanium dioxide precursor has been developed, characterized, and its decomposition products evaluated as electrode materials. Initial studies on the salt $(H_2DABCO)(TiO(C_2O_4)_2) \cdot 2H_2O$ show decomposition to an amorphous material below 400° C. with surprisingly good electrochemical activity alone, in an intimate mixture with carbon, and in a blend with $Li_4Ti_5O_{12}$. The crystalline titanium dioxide (anatase) materials isolated at higher temperatures showed typical electrochemical performance when coated with carbon compared to literature samples. The sample isolated at 50° C. had relatively low capacity possibly due to interstitial atoms blocking the main diffusion channel.

Figure 9:
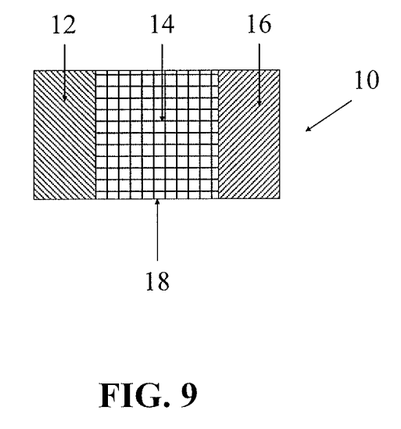
FIG. 9 schematically illustrates an electrochemical cell of the present invention.
Figure 10:
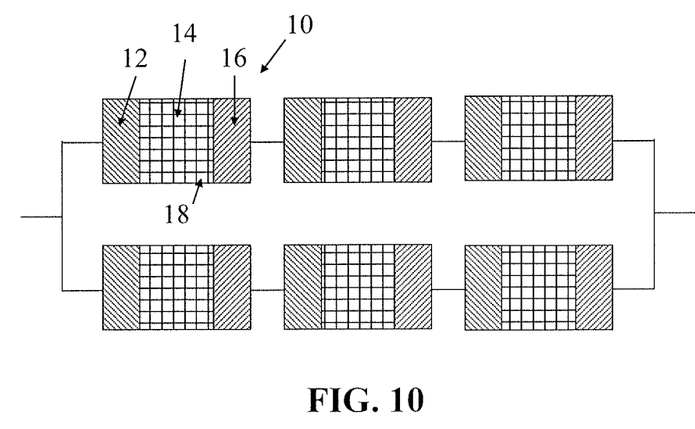
FIG. 10 schematically illustrates a battery of the present invention comprising a plurality of the electrochemical cells shown in FIG. 9.

This invention, therefore, relates to electrodes for non-aqueous electrochemical lithium cells and batteries. A schematic illustration of such a lithium or lithium ion cell shown schematically in FIG. 9. The cell is represented by the numeral 10 having a negative electrode 12 separated from a positive electrode 16 by an electrolyte 14, all contained in an insulating housing 18 with suitable terminals (not shown) being provided in electronic contact with the negative electrode 12 and the positive electrode 16. Binders and other materials normally associated with both the electrolyte and the negative and positive electrodes are well known in the art and are not described herein, but are included as is understood by those of ordinary skill in this art. FIG. 10 shows a schematic illustration of one example of a battery in which two strings of electrochemical lithium cells, described above, are arranged in parallel, each string comprising three cells arranged in series.

While there has been disclosed what is considered to be the preferred embodiments of the present invention, it is understood that various changes in the details may be made without departing from the spirit, or sacrificing any of the advantages of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

[1] M. A. Reddy, V. Pralong, U. V. Varadaraju, B. Raveau, *Electrochem. Sol. State Lett.*, 11 (2008) A132.
[2] J. Wang, J. Polleux, J. Lim, B. J. Dunn, *Phys. Chem. C*, 111 (2007) 14925.
[3] P. G. Bruce, B. Scrosati, J.-M. Tarascon, *Angew. Chem. Intl. Ed.*, 47 (2008) 2930.
[4] A. S. Arico, P. G. Bruce, B. Scrosati, J.-M. Tarascon, W. van Schalkwijk, *Nature Materials*, 4 (2005) 366.
[5] G. Sudant, E. Baudrin, D. Larcher, J.-M. Tarascon, *J. Mater. Chem.*, 15 (2005) 1263.
[6] M. Fernandez-Garcia, C. Belver, J. C. Hanson, X. Wang, J. A. Rodriguez, *J. Am. Chem. Soc.*, 129 (2007) 13604.
[7] R. A. Armstrong, G. Armstrong, J. Canales, R. Garcia, P. G. Bruce, *Adv. Materials*, 17 (2005) 862.
[8] C. H. Jiang, M. D. Wei, Z. M. Qi, T. Kudo, I. Honma, H. S. Zhou, *J. Power Sources*, 166 (2007) 239.
[9] M. Latroche, L. Brohan, R. Marchand, M. Tournoux, *J. Sol. State Chem.*, 31 (1989) 78.
[10] L. D. Noailles, C. S. Johnson, J. T. Vaughey, M. M. Thackeray *J. Power Sources*, 81-82 (1999) 259.
[11] Y. S. Hu, L. Kienle, Y. G. Guo, J. Maier, *Adv. Mater.*, 18 (2006) 1421.
[12] M. A. Reddy, M. S. Kishore, V. Pralong, U. V. Varadaraju, B. Raveau, *Electrochem. Sol. St. Lett.*, 10, (2007) A29.
[13] M. A. Reddy, M. S. Kishore, V. Pralong, V. Caignaert, U. V. Varadaraju, B. Raveau, *Electrochemistry Comm.*, 8 (2006) 1299.
[14] C. Di Valentin, G. Pacchioni, A. Selloni, S. Livraghi, E. Giamello, *J. Phys. Chem. B*, 109 (2005) 11414.
[15] K. S. Rane, R. Mhalsiker, S. Yin, T. Sato, K. Cho, E. Dunbar, P. Biswas, *J. Sol. State Chem.*, 179 (2006) 3033.
[16] S. Nordlinder, L. Nyholm, T. Gustafsson, K. Edström, *Chem. Mater.*, 18 (2006) 495.
[17] X. Li, Y. Xiong, Z. Li, Y. Xie, *Inorg. Chem.*, 45 (2006) 3493.
[18] Y. V. Kolen'ko, A. A. Burukhin, B. R. Churagulov, N. N. Oleinikov, *Inorg. Mater.*, 40 (2004) 822.
[19] E. M. Sorenson, S. K. Barry, H. K. Jung, J. R. Rondinelli, J. T. Vaughey, K. R. Poeppelmeier, *Chem. Mater.*, 2006, 18, 482.
[20] C. D. May, J. T. Vaughey, *Electrochem. Comm.*, 6 (2005) 1075.
[21] C. H. Chen, J. T. Vaughey, A. N. Jansen, D. W. Dees, A. J. Kahaian, T. Goacher, M. M. Thackeray, *J. Electrochem. Soc.*, 148 (2001) A102.
[22] A. Fester, W. Bensch, M. Trömel, *Inorg. Chim. Acta*, 193 (1992) 99.
[23] A. Fester, W. Bensch, M. Trömel, *Acta Cryst. C*, 50 (1994) 850.
[24] X. L. Yao, S. Xie, C. H. Chen, Q. S. Wang, J. H. Sun, Y. L. Li, S. X. Lu, *Electrochimica Acta*, 50 (2005) 4076.
[25] H. Furukawa, M. Hibino, I. Honma, *J. Electrochem. Soc.*, 151 (2004) A527.
[26] M.-C. Tsai, J.-C. Chang, H.-S. Sheu, H.-T. Chiu, C.-Y. Lee, *Chem. Materials*, 21 (2009) 499.

[27] A. K. Padhi, K. S. Nanjunadaswamy, J. B. Goodenough, *J. Electrochem. Soc.,* 144 (1997) 1188.
[28] M. M. Doeff, Y. Q. Yu, F. McLarnon, R. Kostecki, *Electrochem. Sol. St. Letters,* 6 (2003) A207.
[29] C. R. Sides, F. Croce, V. Young, C. R. Martin, B. Scrosati, *Electrochem. Sol. St. Letters,* 8 (2005) A484.

The embodiments of the invention in which an exclusive property or privilege is claimed are defined as follows:

1. An anode for a lithium or lithium ion electrochemical cell, the anode comprising a particulate amorphous titania/carbon composite material comprising about 40 to about 50 percent by weight of amorphous titania and about 50 to about 60 percent by weight of a carbonaceous material coating the titania; wherein the amorphous titania is free from detectable crystalline forms of titania as determined by powder X-ray diffraction techniques.

2. The anode of claim 1, which further comprises $Li_4Ti_5O_{12}$, additional carbon, or a combination thereof, blended with the composite material.

3. An electrochemical cell comprising the anode of claim 1, a cathode, and a lithium ion-containing electrolyte therebetween.

4. The electrochemical cell of claim 3, wherein the electrolyte comprises a lithium salt in a non-aqueous liquid medium.

5. A battery comprising a plurality of electrochemical cells of claim 3, arranged in series, in parallel, or both.

* * * * *